United States Patent
Garner et al.

(10) Patent No.: US 9,950,088 B2
(45) Date of Patent: Apr. 24, 2018

(54) HARD SURFACE DISINFECTION SYSTEM AND METHOD

(71) Applicant: Surfacide, LLC, Waukesha, WI (US)

(72) Inventors: Michael Scott Garner, North Barrington, IL (US); Thomas Smigelski, Lake Zurich, IL (US); Timothy Mathew G. Escolin, Chicago, IL (US); Waldemar John Lyslo, Naperville, IL (US)

(73) Assignee: Surfacide, LLC, Waukesha, WI (US)

( * ) Notice: Subject to any disclaimer, the term of this patent is extended or adjusted under 35 U.S.C. 154(b) by 0 days.

(21) Appl. No.: 15/384,575

(22) Filed: Dec. 20, 2016

(65) Prior Publication Data

US 2017/0100500 A1    Apr. 13, 2017

Related U.S. Application Data

(63) Continuation of application No. 14/687,821, filed on Apr. 15, 2015, now Pat. No. 9,555,144, which is a continuation of application No. 13/756,368, filed on Jan. 31, 2013, now Pat. No. 9,023,274.

(60) Provisional application No. 61/593,182, filed on Jan. 31, 2012.

(51) Int. Cl.

| | |
|---|---|
| *A61L 2/00* | (2006.01) |
| *A62B 7/08* | (2006.01) |
| *G01N 23/00* | (2006.01) |
| *A61N 5/00* | (2006.01) |
| *A61L 2/24* | (2006.01) |
| *A61L 2/10* | (2006.01) |

(52) U.S. Cl.
CPC ........ *A61L 2/24* (2013.01); *A61L 2/10* (2013.01); *A61L 2202/14* (2013.01); *A61L 2202/25* (2013.01)

(58) Field of Classification Search
CPC ..... A61L 2/00; A61L 9/00; A61L 9/18; A61L 9/20
USPC ............ 422/1, 24, 121, 186.05; 250/454.11, 250/455.11, 492.1
See application file for complete search history.

(56) References Cited

U.S. PATENT DOCUMENTS

| | | | |
|---|---|---|---|
| 4,115,280 A | 9/1978 | Pratt, Jr. | |
| 5,517,388 A | 5/1996 | Hutchisson | |
| 6,132,784 A | 10/2000 | Brandt et al. | |
| 6,524,529 B1 * | 2/2003 | Horton, III | A61L 2/10 210/636 |
| 6,656,424 B1 | 12/2003 | Deal | |
| 7,612,492 B2 | 11/2009 | Lestician | |
| 7,923,707 B2 | 4/2011 | Garcia et al. | |
| 8,029,739 B2 | 10/2011 | Field et al. | |
| 8,110,819 B2 | 2/2012 | Boyarski et al. | |

(Continued)

FOREIGN PATENT DOCUMENTS

| | | |
|---|---|---|
| CN | 1489479 A | 4/2014 |
| DE | 7223023 U | 12/1972 |
| JP | 58-77749 B2 | 3/2016 |

*Primary Examiner* — Monzer R Chorbaji
(74) *Attorney, Agent, or Firm* — Inskeep IP Group, Inc.

(57) ABSTRACT

A system and method for disinfecting hard surfaces in an area such as a hospital room including a light source emitting UV light and a reflector mounted behind the light source for concentrating and directing the light toward a target. The light source and reflector rotate to direct the concentrated beam around a room, thereby making more efficient use of the energy being emitted.

20 Claims, 7 Drawing Sheets

(56) References Cited

U.S. PATENT DOCUMENTS

| | | |
|---|---|---|
| 2002/0085947 A1* | 7/2002 | Deal .................. A61L 2/10 422/24 |
| 2002/0100878 A1 | 8/2002 | Summers et al. |
| 2003/0030011 A1 | 2/2003 | Brown et al. |
| 2003/0146082 A1 | 8/2003 | Gibson et al. |
| 2005/0022330 A1 | 2/2005 | Park et al. |
| 2006/0284109 A1 | 12/2006 | Scheir et al. |
| 2007/0053188 A1 | 3/2007 | New et al. |
| 2007/0231192 A1 | 10/2007 | Jung et al. |
| 2009/0143842 A1 | 6/2009 | Cumbie et al. |
| 2009/0184268 A1 | 7/2009 | Garcia et al. |
| 2010/0104471 A1 | 4/2010 | Harmon et al. |
| 2011/0168898 A1 | 7/2011 | Statham et al. |
| 2011/0215261 A1 | 9/2011 | Lyslo et al. |

\* cited by examiner

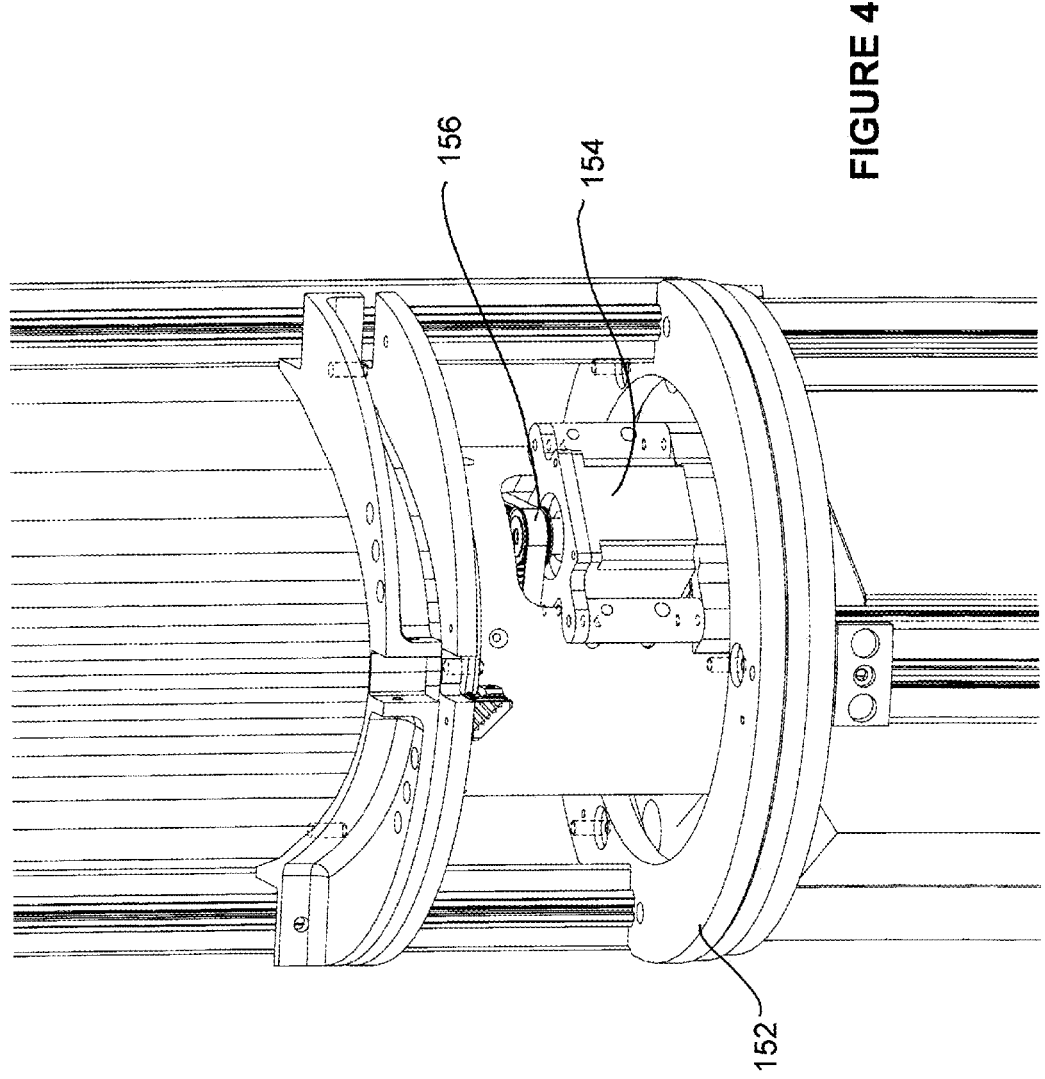

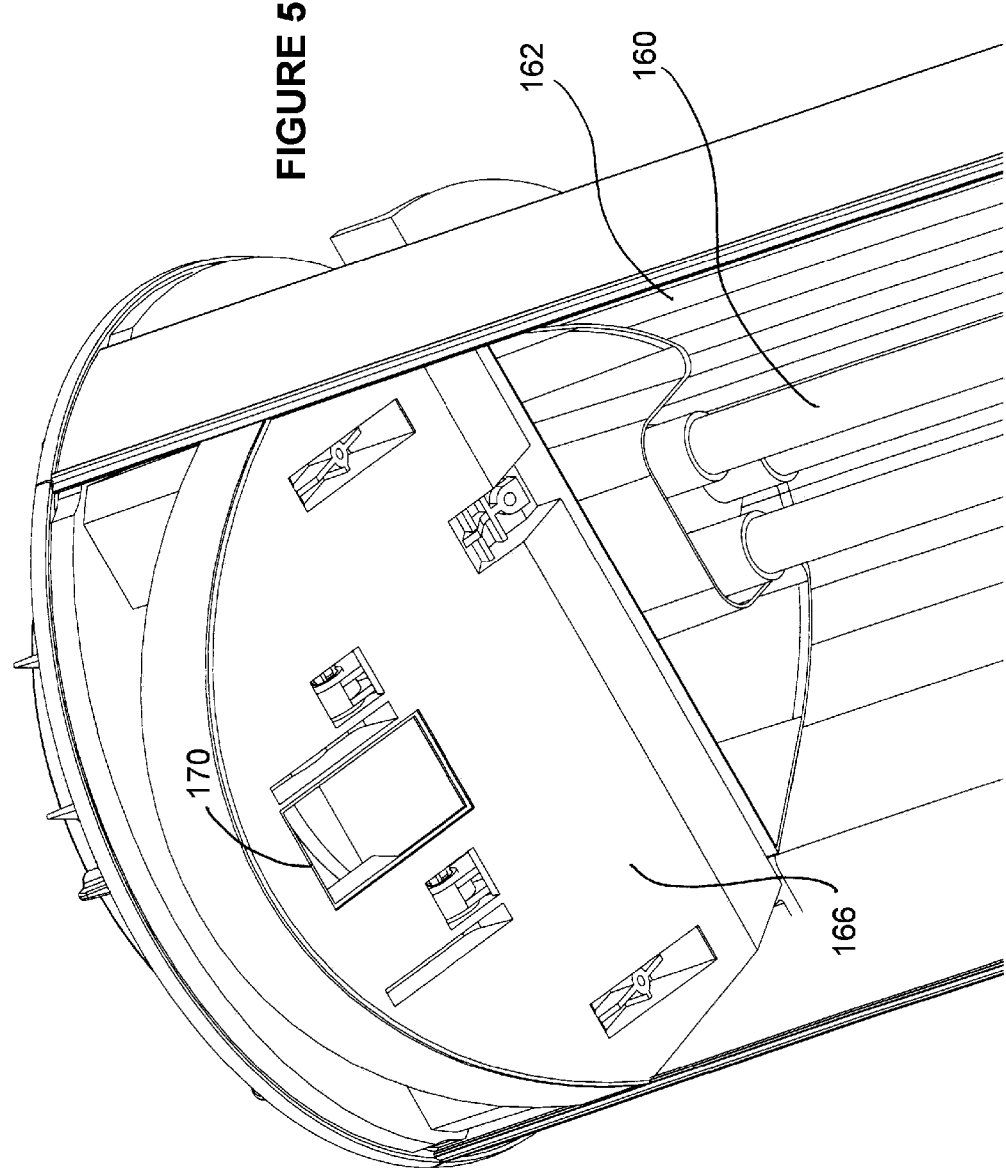

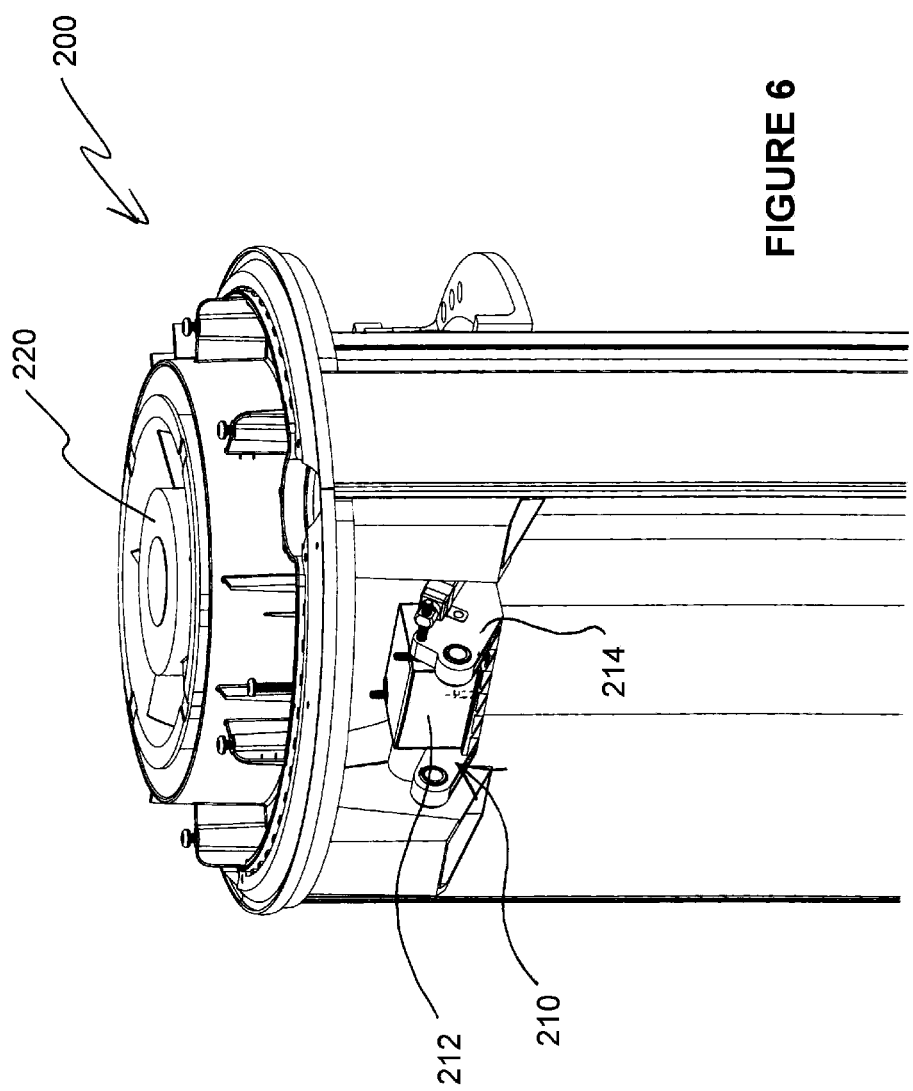

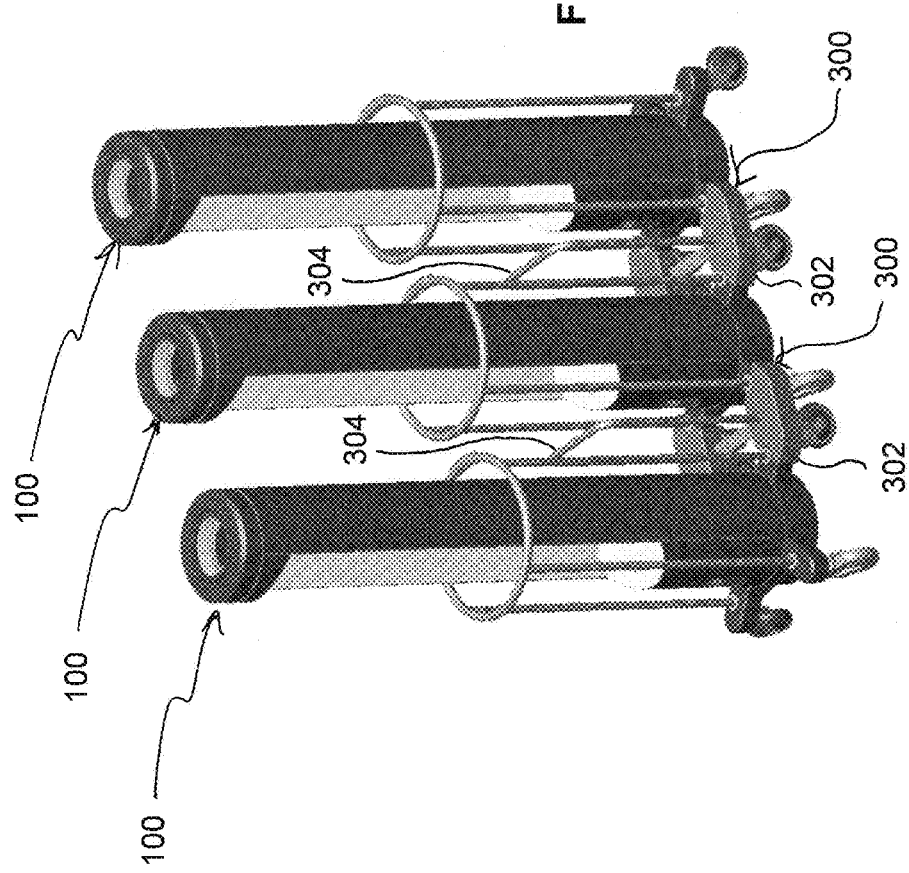

HARD SURFACE DISINFECTION SYSTEM AND METHOD

RELATED APPLICATIONS

This application is a continuation of and claims priority to U.S. patent application Ser. No. 14/687,821 filed Apr. 15, 2015 entitled Hard Surface Disinfection System And Method, which is a continuation of and claims priority to U.S. patent application Ser. No. 13/756,368 filed Jan. 31, 2013 entitled Hard Surface Disinfection System And Method, which claims priority to U.S. Provisional Application Ser. No. 61/593,182 filed Jan. 31, 2012, entitled Hard Surface Disinfection System And Method, both of which are hereby incorporated herein by reference in their entireties.

BACKGROUND OF THE INVENTION

Contrary to the progress made in overall healthcare, the problems associated with health care-associated infections have grown steadily worse. Furthermore, the emergence of multi-drug resistant bacteria and spore "Super Bugs" and their presence in the hard surface environment are recognized as a significant threat in the transmission of infectious disease and associated mortality. Numerous scientifically peer-reviewed studies support the role of the environment in disease transmission. In recognition of this data, thorough disinfection of hard surfaces is an effective and evidence-based way to reduce the presence of these organisms that cause infections and mortality.

Published data reviewing the effectiveness of health care cleaning indicate that greater than 50% of patient room surfaces are not effectively cleaned and/or disinfected after a patient is discharged from the institution. Similar data reflect cleaning proficiency in non-health care environments. As a result, clinicians, health care personnel, visitors, and patients come in contact with bacteria or spores that remain in the room from a prior patient.

Introducing UV-C energy is an evidence-based way to manage the presence of bacteria and spore—including multi-drug resistant organisms. Disinfecting hard surfaces, such as those found in patient areas, can be performed by exposing the hard surfaces to UVC energy that is harmful to micro-organisms such as bacteria, viruses, fungi and spore. Ultraviolet germicidal irradiation (UVGI) is proven sterilization method that uses ultraviolet (UV) energy at sufficiently short wavelengths to break-down and eradicate these organisms. It is believed that the short wavelength radiation destroys organisms at a micro-organic level. It is also believed that UV energy works by destroying the nucleic acids in these organisms, thereby causing a disruption in the organisms' DNA. Once the DNA (or RNA) chain is disrupted, the organisms are unable to cause infection.

In addition to the effectiveness described above, there are advantages to using UV-C energy alone or in concert with other disinfection modalities. UV-C requires only electricity; there is no off-gassing of chemicals frequently associated with chemical based products. In the event a room must be occupied immediately, the introduction of UV-C energy can be immediately terminated and the room immediately occupied. Alternative disinfection modalities, on the other hand, often result in lingering chemicals or agents that must be cleared from the room prior to entry. UV-C energy leaves no residue, does not require drying time, cannot be spilled, requires little manpower to apply, requires very little skill on the part of the operator, and uses long-lasting bulbs that require very little inventory management.

Using UV-C energy to disinfect hard surfaces does present some unique problems. For example, two primary challenges impact efficacy and energy delivery of UV-C energy: shadows and distance. UV-C emitters may not be able to eradicate bacteria in shadowed areas because the energy is delivered along a line-of-sight. Though reflected UV-C light may have some disinfecting ability, the amount of reflected energy depends on the surface from which the light is reflected and cannot be relied upon to adequately disinfect a shadowed area. As such, shadowed areas must be eliminated for effective disinfection. In addition, the UV-C emitting source may itself create shadows. As such, one must consider address these shadows for effective delivery of UV-C energy.

Second, the attempt to introduce UV-C energy to a space is dramatically impacted by the Inverse Square Law. This Law states that the intensity of the energy delivered to a surface is proportional to the inverse of the square of the distance between the energy source and the object. In other words, the energy received from the UV emitting source decreases exponentially as the distance is increased. Thus, if one object is twice as far away from a light source as another object, the further object receives only one quarter the energy as the closer object. Knowing specific energy levels are required to eradicate specific organism, this can dramatically impact efficacy.

Third, UV light sources strong enough to kill bacteria can draw a substantial amount of electricity and generate heat.

As such, there is a need for a UV hard-surface disinfection system that exploits the advantages of UV energy, while also addressing the aforementioned problems.

More specifically, there is a need for a UV hard-surface disinfection system that maximizes the effectiveness of the energy being emitted from its bulbs while eliminating shadows and reaching all surfaces in a treated area despite fall-off due to distances from the light source(s).

SUMMARY OF THE INVENTION

One aspect of the present invention provides a UV hard-surface disinfection system that is able to disinfect the hard surfaces in a room, while minimizing missed areas due to shadows. In one embodiment, a system is provided that includes multiple UV light towers. These towers can be placed in several areas of a room, or moved around during treatment, such that nearly all shadowed areas are eliminated.

Another aspect of the invention provides a UV hard-surface disinfection system that maximizes the efficacy of the light being emitted by including a reflector that focuses the light in a given direction, thereby ensuring that enough light hits a surface to provide an effective bacteria killing dose, and also increasing the effective range of the UV bulbs.

Another aspect of the invention provides a UV hard-surface disinfection system that includes a motorized reflector that rotates around a bulb or bulbs, such that the light emitted from the lamps is not only focused and concentrated, but it is also rotated around the room being treated, thus maximizing the utility of the energy used and eliminating shadows that may be created by the device itself Another aspect of the invention provides a cooling fan used to cool the UV bulbs, thereby increasing the life of the bulbs and managing optimal temperature for optimal output.

In yet another aspect of the present invention there is provided a UV disinfection system that minimizes UV light exposure to humans during operation. In a preferred embodiment, the system is able to be controlled remotely, such that during activation of the system, no operator is present in the room.

Another aspect of the invention provides a system in which one or all towers are outfitted with safety devices that cut power to all towers in the event that a person enters the room. More preferably, the safety device includes motion-detecting capability, such that the safety shutdown response is automatic. Examples of motion-detection sensors include infra-red sensor and laser scanners.

Another aspect of the present invention provides a linking connector that is constructed and arranged to join two towers together. Multiple linking connectors may be used to create a train of towers used to transport a plurality of towers. The advantage of this linkage connector is the UV-C emitters can be easily moved from each desired treatment area while maintaining critical hallway egress to ensure building codes are not breached by the presence of other equipment. The connector may be operated and positioned easily by a single operator. Alternatively, the towers may be linked together with the connector to form a chain. This embodiment allows the towers to support themselves continuously, while being transported by pushing or pulling the emitters. This embodiment also allows the use of a hand-cart attachment, which provides a solution to moving all of the units from one room to another without requiring that they be moved individually.

Another aspect of the invention provides a scanning system that scans a room to be treated and determines how long the system must be energized in order to effectively treat the room.

Another aspect of the invention provides a system whereby multiple towers can detect each other and their respective locations in a room, as well as other objects, and the towers can then use this information to compute exposure times that are inversely proportional to these distances.

Another aspect of the invention provides an algorithm that adjusts the speed of rotation of a reflector/lamp combination to achieve desired energy densities on room surfaces. This differential rotation of the lamp/reflector pair allows towers to normalize exposure on room surfaces, thereby ensuring that all surfaces achieve approximately equal exposure. This results in minimum total exposure times to treat a room or an area of a room. The algorithm further factors the locations of other towers and the energy those towers are contributing to the energy falling into any given area in the room. The exposure times are then adjusted for each tower to account for the additive exposure from multiple towers to result in a minimized exposure time used to sanitize the room.

As such, the present invention provides the following: a device for disinfecting an area comprising: a base assembly; at least one emitter of energy attached to said base assembly; a reflector proximally associated with said emitter; wherein said reflector directs energy from said emitter onto an area to be disinfected; and a motor configured to rotate said reflector relative to said base assembly.

In one embodiment, the base assembly comprises a fan.

In this or another embodiment, the base assembly comprises said motor.

In this or another embodiment, the at least one emitter of energy comprises at least one emitter of ultraviolet light.

In this or another embodiment, the at least one emitter of ultraviolet light comprises at least one UV-C lamp.

In this or another embodiment, the base assembly comprises an antenna usable to establish communication with a remote control device.

In this or another embodiment, the antenna comprises an antenna useable for communication using Bluetooth® wireless technology.

In this or another embodiment, the reflector comprises a parabolic reflector.

The present invention also provides a method of disinfecting a designated area comprising: placing at least one emitter of energy in a room, said emitter configured to emit disinfecting energy in a form of a beam; rotating said beam in a circle until a desired amount of energy has been delivered to surfaces in said room.

In this or another embodiment, the method further comprises controlling a rate at which said beam rotates based on distances measured from said emitter to various objects to be disinfected in said room.

In this or another embodiment, placing at least one emitter of energy in a room comprises placing a plurality of emitters of energy in a room.

In this or another embodiment, controlling rates at which beams of each of said plurality of emitters rotate based on distances measured from said emitters to various objects to be disinfected in said room.

In this or another embodiment, controlling rates at which beams of each of said plurality of emitters rotate is further based on distances measured between said plurality of emitters.

The present invention also provides a system for disinfecting an area comprising: a plurality of devices, each comprising: a base assembly; at least one emitter of energy attached to said base assembly; a reflector proximally associated with said emitter; wherein said reflector directs energy from said emitter onto an area to be disinfected; and a motor configured to rotate said reflector relative to said base assembly.

In this or another embodiment each of said plurality of devices further comprises a sensor usable to determine distances to objects surrounding said device.

In this or another embodiment each of said plurality of devices further comprises a sensor usable to determine distances to other of said plurality of devices.

In this or another embodiment the system further comprises link connectors usable to join two of said plurality of devices together.

In this or another embodiment each of said plurality of devices comprises an electronic control circuit that controls a rate of rotation of said reflector via said motor.

In this or another embodiment said rate of rotation is calculated based on locations of other of said plurality of said devices.

In this or another embodiment each of said plurality of said devices comprises an antenna usable to communication with a remote controller for receiving instructions therefrom.

BRIEF DESCRIPTION OF THE FIGURES

FIG. 4 is a perspective view of a reflector motor of an embodiment of the present invention;

FIG. 5 is a perspective views of an upper portion of an embodiment of the present invention;

FIG. 6 is a perspective view of an upper portion of an embodiment of the present invention;

FIG. 7 is a perspective view of three devices of the invention connected together to form a chain of devices for transport purposes.

DESCRIPTION OF EMBODIMENTS

Figure 1:
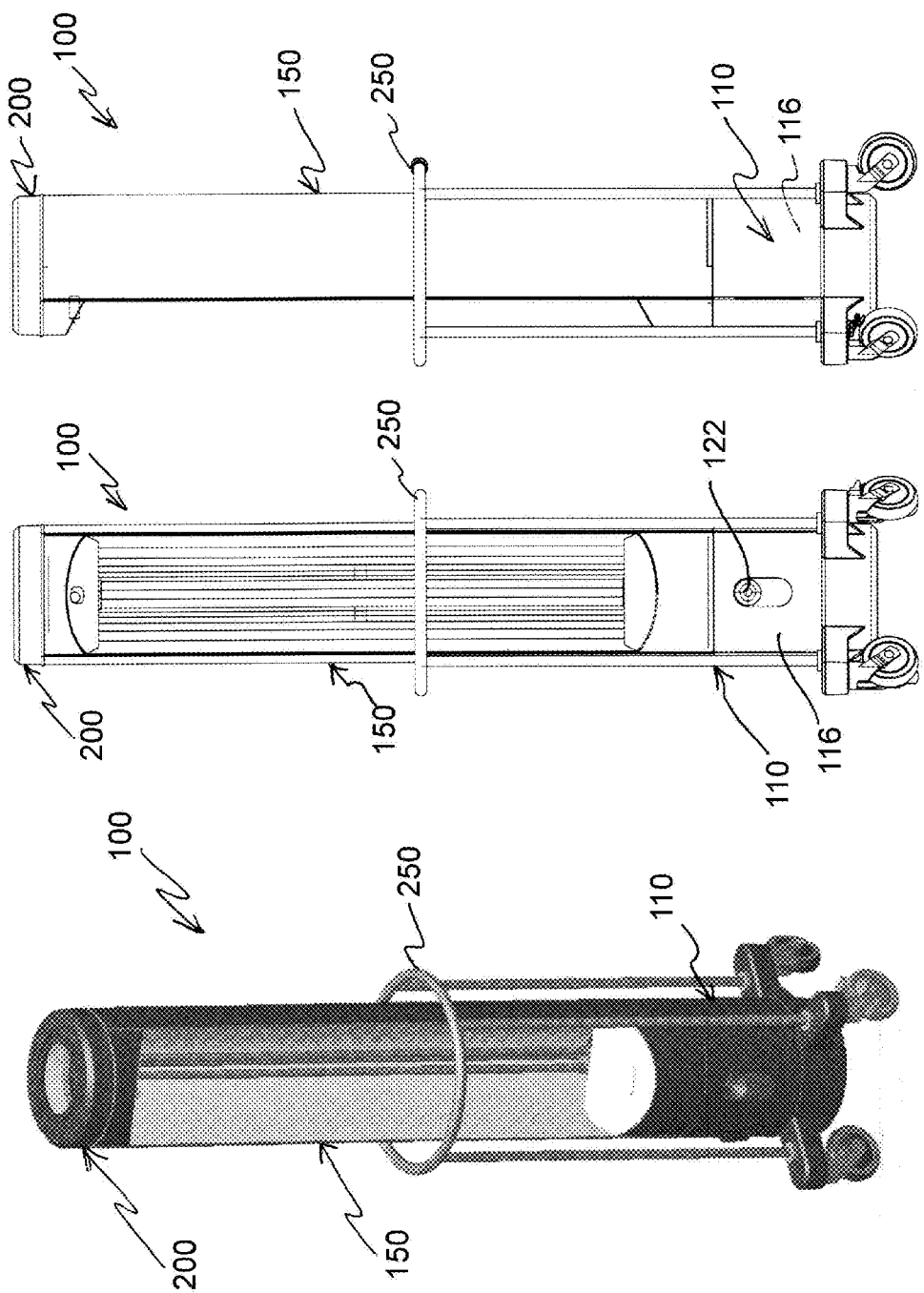
FIG. 1a is a perspective view of an embodiment of the present invention
FIG. 1b is an elevation view of an embodiment of the present invention.
FIG. 1c is a side view of an embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Referring now to FIGS. 1a-c, there is shown an embodiment of a device 100 of the invention. Device 100 is a light tower that generally includes a base assembly 110, a lamp assembly 150, a cap assembly 200, and a hand rail 250. The device 100 is configured for use with a computer application for controlling one or more devices. The application is downloadable and useable on a portable device such as a smart phone or tablet. It is to be understood that in use, it is possible to use several devices 100 simultaneously in order to treat an area large enough to merit the use of more than one device 100.

Figure 2:
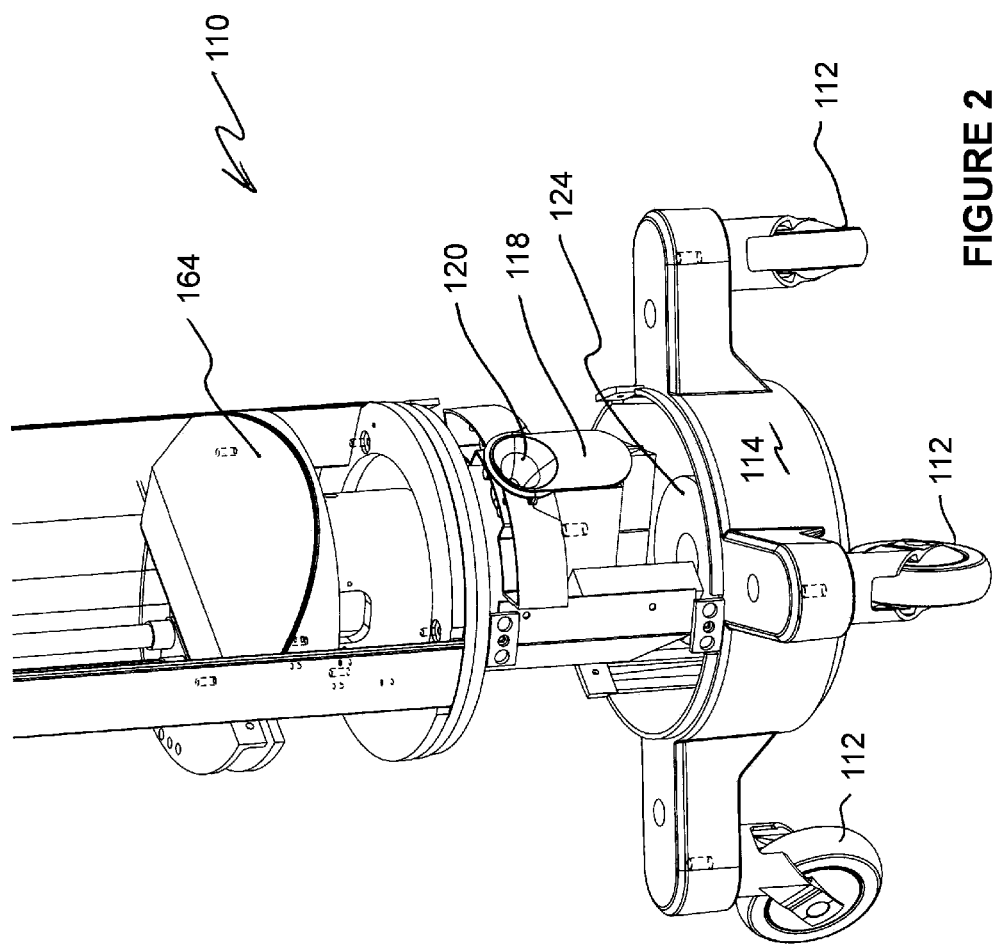
FIG. 2 is a perspective view of a base of an embodiment of the present invention with a cover removed.

Referring now to FIG. 2, there is shown an embodiment of a base assembly 110 of the invention. Beginning at the bottom of the base assembly 110, the device 100 includes at least three, preferably four or more wheels 112. The wheels 112 are preferably mounted on swiveling casters such that the device 100 may be moved easily from room to room during a cleaning operation. The wheels are mounted on a base housing 114, which includes a removable panel 116, shown in FIG. 1 but removed in FIG. 2 to show the parts contained therein.

In an alternate embodiment, wheels 112 are powered and directed by a drive unit (not shown) such as a motor. The motor is either controlled remotely by an operator or locally by an onboard navigation system. It is contemplated that the scanning system (discussed below) provides navigational input to the navigation system, allowing the device 100 to move around the room during the disinfection process in a computed manner calculated to eliminate shadow areas.

An aperture in the removable panel 116 is provided to expose an antenna 118, useable to communicate with a device, such as a smartphone, utilizing the control application. The antenna 118 may be configured to support any wireless communication technology such as IR, radio waves, WLAN, Wi-Fi, or Bluetooth®. Wireless is preferred to tethered as the device 100 is preferably operated in a room without human presence, as UV radiation can be harmful to humans. The antenna 118 is in data-flow communication with a control circuit 119.

Just above the antenna 118 is a portal 120 for a retractable cord 122 (see FIG. 1). The cord 122 may be collected on a spring-loaded, ratcheting spool below the portal 120.

Also below the portal, centered in the bottom of the base assembly, is a fan 124. Fan 124 works in conjunction with a fan in the cap assembly 200 (discussed below), to create a steady stream of cooling air through the lamp assembly 150.

Figure 3:
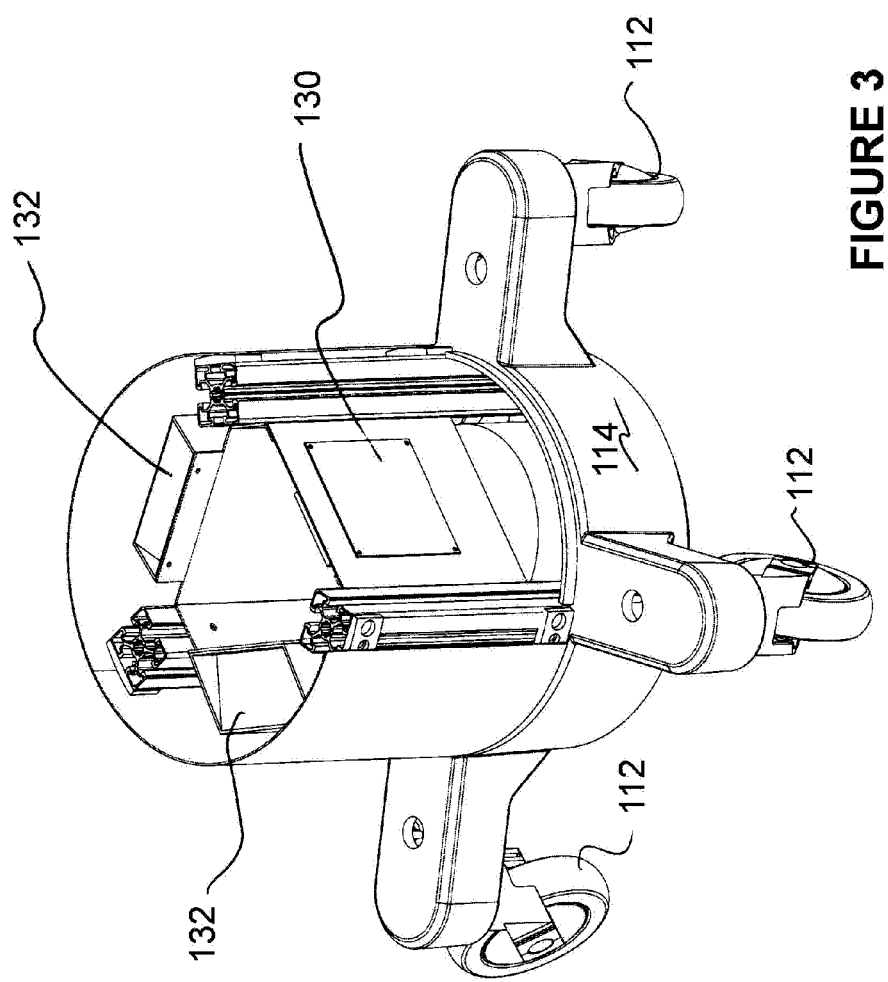
FIG. 3 is a perspective view of a base of an embodiment of the present invention with some components removed to show inner components.

FIG. 3 shows the base assembly 110 with some of the components removed so that the electronic control circuit board 130 and the lamp ballasts 132 are shown. The control circuit board 130 runs an algorithm that allows multiple devices 100 to detect each other and their respective locations in a room, as well as other objects, and the control circuit board 130 then uses this information to compute exposure times that are inversely proportional to these distances.

The control circuit board 130 also controls motor 154 (discussed below) to adjust the speed of rotation of the lamp assembly 150 to achieve desired energy densities on room surfaces. This differential rotation of the lamp assembly 150 allows devices 100 to normalize exposure on room surfaces, thereby ensuring that all surfaces achieve approximately equal exposure. This results in minimum total exposure times to treat a room or an area of a room. The algorithms run by the circuit board 130 further factor the locations of other devices 100 and the energy those devices 100 are contributing to the energy falling into any given area in the room. The exposure times are then adjusted for each device 100 to account for the additive exposure from multiple towers to result in a minimized exposure time used to sanitize the room.

The base assembly 110 is attached to the lamp assembly 150 with a swivel connector 152, best shown in FIG. 4. The swivel connector 152 allows the lamp assembly 150 to rotate in relation to the base assembly 110. A motor 154 is mounted on the base assembly 110 and attached via a drive mechanism 156 to the lamp assembly 150, such that the motor 154, when activated, causes rotation of the lamp assembly 150 relative to the base assembly 110. The drive mechanism 156 is shown as a belt-drive in FIG. 4, but one skilled in the art would recognize that motors can be configured to drive objects using gears, belts, chains, worm-drives, or other mechanisms, all considered to be included as embodiments of the invention.

The lamp assembly 150 also includes at least one lamp 160, as seen in FIG. 5. The number of lamps 160 may be determined by the intended application and desired bulbs available. The embodiment shown in FIG. 5 shows three lamps 160. In one or more embodiments of the invention, the lamps emit UV-C light. Though the lamps 160 shown utilize existing fluorescent UV-C technology, one skilled in the art will realize that advancements in UV-C lamps could result in a variety of lamps being used with the invention.

Behind the lamps 160 is a reflector 162. The reflector 162 wraps around the lamps 160 in order to focus and concentrate the light emitted from the lamps 160 in a desired direction. The reflector 162 may be parabolic, catenary, semi-circular, circular, or other curves, depending on the desired reflective result and/or the placement of the lamps. For example, a parabolic reflector, with the lamps located approximately close to the parabolic focal point, would result in a relatively narrow, focused (collimated) beam. Such a beam increases the intensity of UV radiation in a desired direction.

If desired, it is possible to incorporate a flatter reflector, such as a semi-sphere or catenary reflector. In this regard, a flexible reflector 162 may be provided that is connected to the device 100 in a manner that allows the curve of the reflector to be adjusted based on the desired application.

Alternatively, beam adjustment or focusing could be accomplished by adjusting the lamp position relative to the reflector to create a "zoom" function that would allow the beam to be either more or less tightly focused.

At the bottom of the lamp assembly 150, a lower planar reflector 164 (FIG. 2) is optionally provided. The planar reflector 164 may be angled downwardly, as shown, to scavenge the UV energy that would otherwise be directed onto the floor, where disinfection is typically less critical, and direct it upward into higher areas of the room.

Similarly, at the top of the lamp assembly 150, is an upper planar reflector 166 (FIG. 5). The upper planar reflector 166, like the lower planar reflector 150, is angled to scavenge the UV energy that would otherwise be directed at the ceiling onto areas where human contact is more likely. The upper planar reflector 166 also includes an aperture 170.

Referring now to FIG. 6, there is shown the cap assembly 200 of the invention. The cap assembly is oriented on top of the lamp assembly 150 and includes a sensor mechanism 210 and a cooling mechanism 220.

The sensor mechanism 210 includes a sensor 212 and a sensor drive mechanism 214. The sensor 212 may be any suitable sensor mechanism. Non-limiting examples include laser sensors, and IR (infra-red) sensors. The sensor 212 is used to scan the room to analyze distances to various surfaces and provide input as to the location of objects in the room. The data provided by the sensor 212 may be used to calculate potential shadow areas as well as necessary treatment times and powers. The sensor 212 may also include a motion detection capability, which detects movement prior to the activation of the devices 100 and aborts the treatment initiation in the event that motion is detected just before the treatment. Sensor 212 is shown in FIG. 6 as a single sensor. However, the sensor 212 may incorporate multiple sensing modalities.

The embodiment shown in FIG. 6 also includes a sensor drive mechanism 214. The sensor drive mechanism 214 attaches the sensor 212 to the cap assembly 200 and moves the sensor 212 up and down through the aperture 170 of the upper planar reflector 166.

The cap assembly 200 also includes a cooling mechanism 220 in the form of a fan. The cooling mechanism 220, when energized, creates airflow around the lamps 160 to draw heat away from them.

FIG. 7 shows three devices 100 connected together with linking connectors 300. Linking connectors 300 include a base 302 and a handle 304. The bases 302 are shaped to be placed over two adjacent casters 112, on either side of the devices 100, totaling four casters, to lock two devices 100 together. The handle 304 provides a place to grab and lift the connector 300 and set it down over the casters 112. Using the linking connectors 300, a chain of devices 100 can be formed, allowing a single person to move multiple devices 100 easily.

Although the invention has been described in terms of particular embodiments and applications, one of ordinary skill in the art, in light of this teaching, can generate additional embodiments and modifications without departing from the spirit of or exceeding the scope of the claimed invention. For example, the device 100 described above includes a lamp assembly 150 that rotates relative to the base assembly 110. However, one skilled in the art would realize that the lamps 160 could be fixed relative to the base assembly 110 and the reflector 162 could be configured to rotate around the lamps 160. Accordingly, it is to be understood that the drawings and descriptions herein are proffered by way of example to facilitate comprehension of the invention and should not be construed to limit the scope thereof.

What is claimed is:

1. A method of disinfecting surfaces comprising:
   using at least one ultraviolet emitting device to determine an amount of light energy necessary to disinfect various surfaces in an area containing said at least one ultraviolet emitting device, said ultraviolet emitting device having at least one ultraviolet bulb, based on the location of the surfaces relative to the at least one ultraviolet emitting device;
   energizing the bulb of the at least one ultraviolet emitting device;
   focusing light from the bulb into a concentrated beam using a reflector;
   moving the beam to the various surfaces by rotating the reflector;
   de-energizing the bulb of the at least one ultraviolet emitting device when the determined amount of light energy has disinfected the various surfaces.

2. The method of claim 1 further comprising:
   collecting data relevant to the disinfection of the various surfaces;
   sending the data to a data storage location.

3. The method of claim 1 wherein moving the beam to the various surfaces by rotating the reflector around the bulb comprises controlling a rate of rotation of the reflector based on the determined amount of light energy necessary to disinfect the various surfaces.

4. The method of claim 3 wherein controlling a rate of rotation of the reflector based on the determined amount of light energy necessary to disinfect the various surfaces comprises varying the rate of rotation of the reflector based on the angular location of the reflector relative to a surface being disinfected.

5. The method of claim 1 wherein determining an amount of light energy necessary to disinfect various surfaces based on the location of the surfaces relative to the at least one ultraviolet emitting device comprises factoring into the determination, light emitted from other ultraviolet devices present in the area.

6. The method of claim 1 wherein determining an amount of light energy necessary to disinfect various surfaces in an area containing at least one ultraviolet emitting device, said ultraviolet emitting device having at least one ultraviolet bulb, based on the location of the surfaces relative to the at least one ultraviolet emitting device comprises determining an amount of light energy necessary to disinfect various surfaces in an area containing a plurality of ultraviolet emitting devices, each having at least one ultraviolet bulb, based on the location of the surfaces relative to each of the ultraviolet emitting devices.

7. The method of claim 6 wherein determining an amount of light energy necessary to disinfect various surfaces containing a plurality of ultraviolet emitting devices, each having at least one ultraviolet bulb, based on the location of the surfaces relative to each of the ultraviolet emitting devices comprises establishing communication between each of the ultraviolet emitting devices.

8. The method of claim 6 wherein determining an amount of light energy necessary to disinfect various surfaces in an area containing a plurality of ultraviolet emitting devices, each having at least one ultraviolet bulb, based on the location of the surfaces relative to each of the ultraviolet emitting devices comprises establishing communication between each of the ultraviolet emitting devices and a remote control.

9. The method of claim 1 wherein determining an amount of light energy necessary to disinfect various surfaces in an area containing at least one ultraviolet emitting device, said ultraviolet emitting device having at least one ultraviolet bulb, based on the location of the surfaces relative to the at least one ultraviolet emitting device comprises mapping the area using a scanner on the ultraviolet emitting device to measure distances from the ultraviolet emitting device to the various objects in the area.

10. The method of claim 1 further comprising de-energizing the bulb of the at least one ultraviolet emitting device if movement is detected in the area.

11. A disinfection system comprising:
a plurality of energy emitting assemblies, each including:
a base assembly;
at least one energy emitter extending from the base emitter and having a longitudinal axis;
an antenna for sending and receiving data;
a control circuit board operably connected to the antenna;
a scanner capable of measuring distances to various objects present in an area;
an algorithm that determines desired exposure times for the various objects based on distance from the various objects to each of the various emitters.

12. The disinfection system of claim 11 wherein said algorithm is incorporated into the control circuit boards of the plurality of energy emitting assemblies.

13. The disinfection system of claim 11 further comprising a remote control communicating with each of the plurality of energy emitting assemblies.

14. The disinfection system of claim 11 wherein each of the plurality of energy emitting assemblies further includes;
a reflector positioned adjacent the energy emitter and shaped to focus energy from the emitter in a direction perpendicular to the longitudinal axis of the energy emitter; and,
a motor operably coupled to the reflector such that the motor rotates the reflector around the emitter in a circle.

15. The disinfection system of claim 14 wherein the motor is controlled by the control circuit board.

16. The disinfection system of claim 15 wherein the control circuit board varies a speed of the motor to cause each of the various objects to receive the desired exposure time determined by the algorithm.

17. A method of disinfecting an area comprising:
using at least one energy emitting device to determine distances from a plurality of surfaces in an area to said at least one energy emitter;
rotating a beam of energy from the at least one energy emitter at various speeds to ensure that all of the plurality of surfaces in the area receive at least a minimum total exposure time based on said distances.

18. The method of claim 17 wherein determining distances from a plurality of surfaces in an area to at least one energy emitter comprises determining distances from a plurality of surfaces in an area to a plurality of energy emitters.

19. The method of claim 18 wherein rotating a beam of energy from the at least one energy emitter at various speeds to ensure that all of the plurality of surfaces in the area receive at least a minimum total exposure time based on said distances comprises:
determining the total exposure time each surface will receive from each of the plurality of energy emitters based on the locations of each of the plurality of energy emitters in the area, the distances of each of the surfaces to each of the plurality of emitters; the rotation speed of the beams of each of the plurality of emitters.

20. The method of claim 17 further comprising recording data concerning the disinfection of the area and sending the data collected to a storage medium.

* * * * *